(12) United States Patent
Slaugenhaupt et al.

(10) Patent No.: US 7,737,110 B2
(45) Date of Patent: Jun. 15, 2010

(54) METHODS FOR ALTERING MRNA SPLICING AND TREATING FAMILIAL DYSAUTONOMIA AND OTHER MECHANISTICALLY RELATED DISORDERS

(75) Inventors: Susan A. Slaugenhaupt, Hingham, MA (US); James F. Gusella, Framingham, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 10/956,601

(22) Filed: Oct. 1, 2004

(65) Prior Publication Data

US 2006/0014763 A1 Jan. 19, 2006

Related U.S. Application Data

(60) Provisional application No. 60/508,465, filed on Oct. 3, 2003, provisional application No. 60/536,287, filed on Jan. 13, 2004.

(51) Int. Cl.
*A61K 38/00* (2006.01)
*A01N 61/00* (2006.01)
*C12N 15/00* (2006.01)
*C12N 15/01* (2006.01)
*C07H 21/04* (2006.01)

(52) U.S. Cl. .................... 514/2; 435/441; 435/440; 536/23.1; 536/24.3

(58) Field of Classification Search ............... None
See application file for complete search history.

(56) References Cited

OTHER PUBLICATIONS

Hims, et al. Therapeutic potential and mechanism of kinetin as a treatment for the human splicing disease familial dysautonomia, J. Mol. Med. 85:149-161, 2007.*

Slaugenhaupt SA, Gusella JF. Familial dysautonomia.Curr Opin Genet Dev. Jun. 2002;12(3):307-11.*
Pavlica et al., "Effects of Benzyladenine on Prokaryotic and Eukaryotic Cells", *Mutation Research*, Apr. 1992, vol. 281, No. 4, pp. 277-282.
Cuajungco et al., Tissue-specific Reduction in Splicing Efficiency of IKBKAP due to the Major Mutation Associated with Familial Dysautonomia, *Am. J. Hum. Genet.*, Mar. 2003, vol. 72, No. 3, pp. 749-758.
PCT Search Report dated Feb. 26, 2007.
Anderson et al., "Tocotrienols Induce IKBKAP Expression: A Possible Therapy for Familial Dysautonomia", Biochem. and Biophys. Res. Comm., Jun. 2003, vol. 36, pp. 303-309.
Anderson et al., "EGCG Corrects Aberrant Splicing of IKAP mRNA in Cells From Patients With Familial Dysautonomia", Biochem. and Biophys. Res. Comm., Oct. 2003, vol. 310, pp. 627-633.
Slaugenhaupt et al., "Rescue of a Human mRNA Splicing Defect by the Plant Cytokinin Kinetin", Human Molecular Genetics, Feb. 2004, vol. 13, No. 4, pp. 429-436.
Gold-von Simon et al., "Kinetin in Familial Dysautonomia Carriers: Implications for a New Therapeutic Strategy Targeting mRNA Splicing," Pediatric Research, 65(3), 341-346 (Mar. 2009)(electronically published ahead of print on Nov. 19, 2008).
Lee et al., "Modeling Pathogenesis and Treatment of Familial Dysautonomia Using Patient-Specific iPSCs," Nature, 461, pp. 402-408, Sep. 17, 2009.

* cited by examiner

*Primary Examiner*—Nancy Vogel
*Assistant Examiner*—Catherine Hibbert
(74) *Attorney, Agent, or Firm*—Kenneth H. Sonnenfeld; Margaret B. Brivanlou; King & Spalding LLP (57) ABSTRACT

This invention relates to methods for altering the splicing of mRNA in cells. In particular, this invention also relates to methods for increasing the ratio of wild type to misspliced forms of mRNA and corresponding encoded proteins in cells possessing a mutant gene encoding either the i) misspliced mRNA corresponding to the mutant protein or ii) a component in the splicing machinery responsible for processing the misspliced mRNA. In addition, this invention relates to treating individuals having a disorder associated with a misspliced mRNA, such as Familial Dysautonomia or Neurofibromatosis 1, by administering to such an individual a cytokinin such as kinetin.

10 Claims, 5 Drawing Sheets

METHODS FOR ALTERING MRNA SPLICING AND TREATING FAMILIAL DYSAUTONOMIA AND OTHER MECHANISTICALLY RELATED DISORDERS

This application claims benefit of provisional application U.S. Ser. No. 60/508,465, filed Oct. 3, 2003 and provisional application U.S. Ser. No. 60/536,287, filed Jan. 13, 2004.

This invention was made with United States Government support under grants from the National Institutes of Neurological Disorders and Stroke. The United States Government has certain rights in this invention.

FIELD OF THE INVENTION

This invention relates to methods for altering the splicing of mRNA in cells. In addition, this invention also relates to methods for correcting the ratio of wild type to mutant spliced forms of mRNA and corresponding encoded proteins in cells possessing a mutant gene encoding either i) the misspliced mRNA corresponding to the mutant protein or ii) a component of the splicing machinery. In addition, this invention relates to treating individuals having a disorder associated with a misspliced mRNA, such as familial dysautonomia, by administering to such an individual a cytokinin such as kinetin.

In particular, the invention relates to enhancing correct mRNA splicing in order to increase cellular levels of normal or wild type IKAP mRNA or protein encoded by a IKBKAP gene in various cell types. The defective splicing of pre-mRNA is a major cause of human disease.

BACKGROUND OF THE INVENTION

Exon skipping is a common result of splice mutations and has been reported in a wide variety of genetic disorders[1], yet the underlying mechanism is poorly understood. Often, such mutations are incompletely penetrant, and low levels of normal transcript and protein are maintained[1]. Familial dysautonomia (FD) (MIM#2239001), also known as Riley Day syndrome or hereditary sensory and autonomic neuropathy III (HSAN-III), is the best-known and most common member of a group of congenital sensory and autonomic neuropathies (HSAN) characterized by widespread sensory and variable autonomic dysfunction (Axelrod F B: (1996) Autonomic and Sensory Disorders. In: *Principles and Practice of Medical Genetics*. 3rd edition, A E H Emory and D L Rimoin eds. Churchill Livingstone, Edinburgh. pp 397-411; Axelrod F B (2002) Hereditary Sensory and Autonomic Neuropathies: Familial Dysautonomia and other HSANs. Clin Auton Res 12 Supplement 1, 2-14). FD affects neuronal development and is associated with progressive neuronal degeneration. Multiple systems are impacted resulting in a markedly reduced quality of life and premature death (Axelrod F B: (1996) Autonomic and Sensory Disorders. In: *Principles and Practice of Medical Genetics*. 3rd edition, A E H Emory and D L Rimoin eds. Churchill Livingstone, Edinburgh. pp 397-411; Axelrod F B (2002) Hereditary Sensory and Autonomic Neuropathies: Familial Dysautonomia and other HSANs. Clin Auton Res 12 Supplement 1, 2-14).

Figure 1:
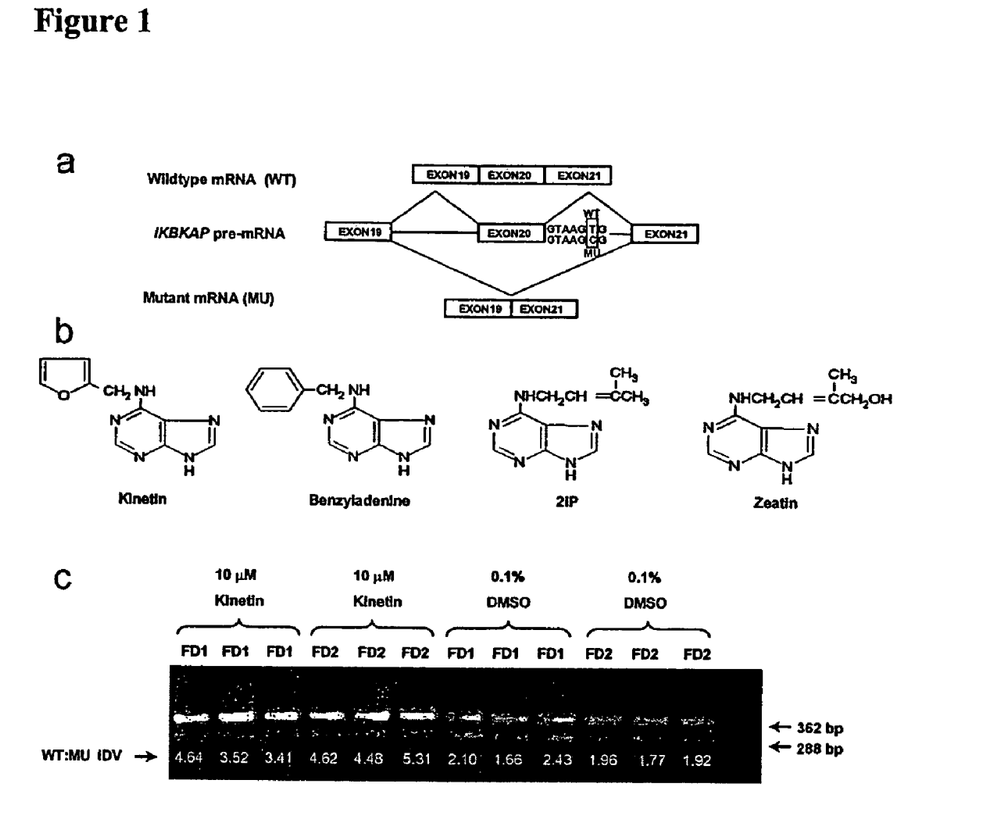

FD is a recessive disorder that has a remarkably high carrier frequency of 1 in 30 in the Ashkenazi Jewish population[5]. FD is caused by mutations in the IKBKAP gene[2,3] (Genbank Accession No. NM_003640), and all cases described to date involve an intron 20 mutation that results in a unique pattern of tissue-specific exon skipping. Accurate splicing of the mutant IKBKAP allele is particularly inefficient in the nervous system. Three FD mutations have been identified in the I-k-B kinase (IKK) complex-associated protein (IKBKAP): IVS20$^{+6T \to C}$, which leads to variable, tissue-specific skipping of exon 20 (FIG. 1a), R696P, and P914L[2,3,6]. All FD patients tested to date carry at least one IVS20$^{+6T \to C}$ mutation, with more than 99.5% being homozygous, and the remainder being heterozygous with either R696P or P914L on the alternate allele.

The IVS20$^{+6T \to C}$ mutation does not cause complete loss of function. Instead, it results in a tissue-specific decrease in splicing efficiency of the IKBKAP transcript; cells from patients retain some capacity to produce normal mRNA and IKAP protein (Slaugenhaupt et al. (2001) Tissue-specific expression of a splicing mutation in the IKBKAP gene causes familial dysautonomia. Am J Hum Genetics 68:598-605). The mRNA is widely distributed. Highest levels are in the nervous system, but substantial amounts are also present in peripheral organs (Mezey et al. (2003) Of splice and men: what does the distribution of IKAP mRNA in the rat tell us about the pathogenesis of familial dysautonomia? Brain Research 983:209). It has been reported previously that all FD tissues tested express both wild-type (WT) and mutant (MU) IKBKAP mRNA[2,4]. The effect of the most common (splicing) mutation varies from tissue to tissue—neuronal tissues seem primarily to express mutant mRNA; somatic tissues express roughly equal levels of normal and mutant mRNA. Accurate measurement of the ratio of the two mRNA species using both densitometry and real-time quantitative PCR has revealed that the levels of WT IKBKAP mRNA vary between tissues and are lowest in central and peripheral nervous systems[4]. This leads to a drastic reduction in the amount of IKAP protein in these tissues.

There are other disorders that are caused, at least in part, by missplicing including Neurofibromatosis 1 (NF1), also known as von Recklinghausen NF or Peripheral NF. NF1 occurs in 1:4,000 births and is characterized by multiple cafe-au-lait spots and neurofibromas on or under the skin. Enlargement and deformation of bones and curvature of the spine may also occur (Riccardi, 1992, *Neurofibromatosis: Phenotype, natural history, and pathogenesis*. 2nd ed. Baltimore: Johns Hopkins University Press). Occasionally, tumors may develop in the brain, on cranial nerves, or on the spinal cord. About 50% of people with NF also have learning disabilities (Chapter 6 in Rubenstein and Korf, 1990, *Neurofibromatosis: a handbook for patients, families, and healthcare professionals*. New York: Thieme Medical Publishers).

The NF1 gene was identified and the protein product characterized in 1990 (Cawthon et al., 1990, Cell 62: 193-201; Wallace et al., 1990, Science 249:181-6). The entire sequence of the expressed NF1 gene has been reported (Viskochil et al., 1993, Annu Rev Neurosci 16: 183-205; Gutmann and Collins, 1993, Neuron 10: 335-43; Genbank Accession No. NM_000267). The gene is has at least 59 exons and codes for a 2818 amino acid protein called neurofibromin. To date, 180 different NF1 mutations have been identified. The NF1 Genetic Analysis Consortium maintains a database of mutations identified in more than 45 collaborating laboratories throughout the world. According to data from the Consortium, the NF1 mutations described to date include 4 chromosomal rearrangements, 89 deletions (14 deletions involving the entire gene, 35 deletions involving multiple exons, and 37 small deletions), 23 insertions (3 large and 20 small), 45 point mutations (29 stop mutations and 16 amino acid substitutions), and 18 intronic mutations affecting splicing, and 4 mutations in 3' untranslated region of the gene. About 30% of NF1 patients carry a splice mutation resulting in the production of one or several shortened transcripts (Vandenbroucke et al., 2002, BMC Genomics 3:13 and Serra et al., 2001, Hum Genet. 108:416-29).

Cytokinins are a class of plant hormones defined by their ability to promote cell division in plant tissue explants in the presence of an auxin, such as indoleacetic acid, and nutrients, including vitamins, mineral salts, and sugar. In promoting cell division of plant cells, cytokinins are active at low concentrations (as low 0.01 parts per million (ppm)), but exhibit activity only in the presence of an auxin. Certain cytokinins, including zeatin and 6-(3,3-dimethylallyl)-aminopurine, also occur as the base moiety components of transfer RNA in yeast, bacterial, animal cells and plant cells. The cytokinin kinetin (6-furfuryl-aminopurine) forms complexes with certain RNA-binding proteins of wheat embryo extracts and appears to promote protein synthesis in plants (see, e.g., Spirin and Ajtkhozhin (1985) Trends in Biochem. Sci., p. 162). Kinetin and other cytokinins are used in conjunction with auxin used in horticulture and in plant tissue culture, such as in the production of plantlets from plant callus tissue. Cytokinins are also used in the production of protein-rich yeast (see e.g., East German Patent No. 148,889 (1981) (Derwent World Patent Index Abstract)) and to augment the growth of microbial cultures (Merck Index, 10th Ed. (1983) Entry 5148, Merck and Co., Rahway, N.J., U.S.A.).

Kinetin belongs to the family of $N^6$—substituted adenine derivatives known as cytokinins, or plant growth factors, that also includes zeatin, benzyladenine and 2iP (FIG. 1b). Kinetin is also known as 6-furfurylaminpurine ($C_{10}H_9N_5$) and has a molecular weight of 215.21 (Soriano-Garcia and Parthsarathy, 1975, Biochem Biophys Res Commun 64:1062-8). Kinetin is currently marketed as an anti-aging ingredient in skin treatments due to its ability to ameliorate aging characteristics in cultured human fibroblasts[8], possibly through anti-oxidant activity[9].

Certain cytokinins have been shown to inhibit the growth of tumor cells in vitro (see, e.g., Katsaros et al. (1987) FEBS Lttrs. 223:97-103). It appears that this effect is mediated via the cytotoxic affects of adenosine analogs, such as the 6-(substituted amino) purine cytokinins, that interfere with tRNA methylating enzymes (Wainfan et al, (1973) Biochem. Pharmacol. 22:493-500). When immortalized fibroblast cells are contacted with adenosine analogs the cultured cells exhibit decreased growth rate and a change in morphology from the normal flattened elongated morphology typical of cultured fibroblasts to a very elongated spindle-shape characteristic of a cytotoxic response. The very elongated shape of immortalized cells exhibiting this response is not shape characteristic of young, healthy, primary cultures of normal diploid fibroblasts.

Kinetin has been shown to be capable of delaying or preventing a host of age-related changes of human skin fibroblasts grown in laboratory culture which has led to its incorporation into topical skin products. West MID (1994) The cellular and molecular biology of skin aging. Arch Dermatol 130:87-95. Fibroblasts, which produce collagen and elastin, have been shown to decrease in number and vitality as skin ages not only in vitro, but also in vivo. The number of fibroblasts decreases at least 50% between birth and the age of 80 years. West MID (1994) The cellular and molecular biology of skin aging. Arch Dermatol 130:87-95. Rattan S I, Clark B F. (1994) Kinetin delays the onset of aging characteristics in human fibroblasts. Biochem Biophys Res Commun 201:665-72. Kinetin has been shown to delay or prevent a range of cellular changes associated with in vitro aging of human skin cells, including alterations in cell morphology, growth rate, size, cytoskeletal organization, macromolecular synthetic activity and accumulation of lipofuscin aging pigments but kinetin did not alter the maximum in vitro life span of human skin cells or their ability to multiply in culture. Rattan S I, Clark B F. (1994) Kinetin delays the onset of aging characteristics in human fibroblasts. Biochem Biophys Res Commun 201:665-72. Thus, kinetin was devoid of activities associated with cellular immortalization, malignant transformation and carcinogenesis. Rattan S I, Clark B F. (1994) Kinetin delays the onset of aging characteristics in human fibroblasts. Biochem Biophys Res Commun 201:665-72.

Using rats as a mammalian model, it has been shown that plant cytokinins can affect lipid peroxidation in erythrocyte, muscle, liver, heart and kidney tissue, Celik I, Tuluce Y, Ozok N. (2002) Effects of indoleacetic acid and kinetin on lipid peroxidation levels in various rat tissues. Turk J Biol 26; 193-196. Celik et al. (2002) showed that kinetin had much less toxicity as compared to indoleacetic acid (IAA), when administered orally to rats. Celik I, Tuluce Y, Ozok N. (2002) Effects of indoleacetic acid and kinetin on lipid peroxidation levels in various rat tissues. Turk J Biol 26; 193-196. It was shown that IAA interacts primarily with the liver and kidney tissue cells, resulting in lipid peroxidation synthesis, whereas kinetin had no such effect in the liver or kidney.

SUMMARY OF THE INVENTION

This invention relates to methods and compositions for increasing the amount of wild type protein encoded by cells possessing a misspliced mRNA due to either a mutation in i) the misspliced mRNA corresponding mutant protein or ii) a component of the splicing machinery. In preferred embodiments, the misspliced mRNA is a mutant mRNA. The increased wild type protein results from contacting cells with or administering to individuals one or more compounds which increases the amount of properly spliced mRNA. In preferred embodiments, the compound is a cytokinin. In a more preferred embodiment, the cytokinin is kinetin, (6-furfurylaminopurine).

In one embodiment of this invention, cells possessing a mutant gene resulting in misspliced mRNA are contacted with a cytokinin which results in an enhanced ratio of correctly spliced mRNA compared to misspliced mRNA.

In another embodiment of this invention, cells or individuals are contacted with a cytokinin (preferably kinetin) to treat neuronal degeneration.

In another embodiment of this invention a cytokinin (preferably kinetin) is administered to an individual with a disorder or disease associated with a mutation resulting in misspliced mRNA.

In a preferred embodiment, individuals with familial dysautonomia (FD) are treated with a therapeutically effective amount of a cytokinin (preferably kinetin) to decrease missplicing of the IKBKAP transcript and increase the ratio of wild type IKAP protein versus mutant IKAP protein. In a specific embodiment, a pharmaceutical composition comprises the therapeutically effective amount of the cytokinin and is administered to a subject suffering or likely to suffer from FD.

In another preferred embodiment, individuals with Neurofibromatosis 1 (NF1) caused by missplicing are treated with a therapeutically effective amount of a cytokinin (preferably kinetin) to decrease missplicing of the NF1 transcript and increase the ratio of wild type neurofibromin protein versus mutant neurofibromin protein. In a specific embodiment, a pharmaceutical composition comprises the therapeutically effective amount of the cytokinin and is administered to a subject suffering or likely to suffer from NF1.

The methods of the invention encompass in vivo and in vitro screening assays to identify compounds that alter the splicing of misspliced mRNA transcripts. In one embodiment, the misspliced mRNA transcript is a mutant IKBKAP mRNA transcript. In a more specific embodiment, the mutant IKBKAP mRNA transcript carries a mutation that is present in a mutant IKBKAP mRNA in a subject with FD. In an even more specific embodiment, the mutant IKBKAP mRNA transcript has the IVS20$^{+6T \rightarrow C}$ mutation. In another embodiment, the misspliced mRNA transcript is a mutant NF1 mRNA transcript. In a more specific embodiment, the mutant NF1 mRNA transcript carries a mutation that is present in a mutant NF1 mRNA in a subject with NF1. Candidate compounds are screened for the ability to alter the splicing of misspliced mRNA transcripts comprising contacting a mammalian cell comprising DNA which comprises the gene (or a fragment or variant thereof) which is misspliced with a candidate compound and determining the amount of misspliced and/or wild type mRNA transcript. In a specific embodiment, candidate compounds are screened for the ability to alter the inclusion of exon 20 of a wild type or mutated IKBKAP gene. In more specific embodiments, the ratio of exon 20 inclusion to exon 20 skipping is determined for spliced IKBKAP mRNA transcripts in the presence and absence of the candidate compound. An alteration in the ratio of exon 20 skipping to exon 20 inclusion indicates that the candidate compound did alter the splicing of the misspliced mRNA.

It is an object of the present invention to provide a compound or compounds which are suitable as therapeutic agent(s) for the treatment of disorders involving missplicing of mRNAs, especially FD and NF1. A further object of the present invention is to provide a process and compositions which are suitable for altering the splicing of mRNA in a mammalian cell.

The present invention provides a composition which is capable of affecting mRNA splicing. In a preferred embodiment, the composition is capable of altering mRNA splicing of the IKBKAP gene. In a specific preferred embodiment, the composition is capable of altering IKBKAP gene splicing by increasing the inclusion of exon 20. In another preferred embodiment, the composition is capable of altering mRNA splicing of the NF1 gene. As such the composition is also useful as a pharmaceutical composition to prevent, manage, and/or treat FD and/or NF1 caused by missplicing according to the methods of the invention.

In some embodiments, the one or more cytokinins used in the methods of the invention are administered to a subject in need thereof in combination with at least one other compound that provides a therapeutic effect. Examples of such other compounds include, but are not limited to, antioxidants (such as (−)-epigallocatechin gallate) and tocotrienols (such as α-tocotrienol, β-tocotrienol, γ-tocotrienol, and δ-tocotrienol).

BRIEF DESCRIPTION OF THE DRAWINGS

FIG. 1 Kinetin significantly increases production of wild-type IKBKAP transcript in FD cells. (a) Schematic diagram illustrating the location of the IVS20$^{+6T \rightarrow C}$ mutation in IKBKAP and the two IKBKAP isoforms produced from this allele in FD patients. (b) Chemical structures of the cytokinins tested in this study: kinetin (6-furfurylaminopurine), benzyladenine (6-benzylaminopurine), 2iP (6-(γ,γ-dimethylallylamino)purine), and zeatin (6-(4-hydroxy-3-methylbut-2-enylamino)purine). (c) RT-PCR analysis of 2 independent FD lymphoblast cell lines, tested in triplicate, following treatment with 10 μM kinetin in 0.1% DMSO or DMSO alone. Previous experiments demonstrated that DMSO has no effect on IKBKAP splicing. WT:MU ratios were determined using the integrated density value (IDV) obtained for each band and are shown beneath each lane. The sizes of the WT (including exon 20) and MU (excluding exon 20) PCR products are indicated on the right. Primer sequences and PCR conditions have been previously described[4].

FIG. 3 Kinetin has no effect on incorporation of exon 31 in the alternatively spliced MYO5A gene (a) schematic diagram illustrating two of the alternative transcripts produced by MYO5A. The primers used for amplification are illustrated by arrows indicated on each isoform. (b) representative example of RT-PCR from FD lymphoblast cells showing no change in the ratio of MYO5A isoforms by kinetin treatment. Nine independent cell lines were tested.

FIG. 5 Kinetin enhances inclusion of exon 20 in both the MU and WT IKBKAP minigene. (a) schematic diagram illustrating the minigene constructs and the location of the IVS20$^{+6T \rightarrow C}$ mutation. Vector specific primers used for RT-PCR analysis are shown. (b) RT-PCR of MU and WT minigene RNA isolated from HEK293 cells following transfection and treatment with kinetin. PCR was performed using the primers T7 and BGH-R. Trace amounts of MU IKBKAP can be seen in the untreated WT lanes. PCR fragment sizes of the two spliced products are shown on the left. (c) RT-PCR of the same RNA in panel (b) using T7 and a primer that spans the 19-21 exon junction known to specifically amplify the MU band[4], showing absence of MU transcript in the WT lane following kinetin treatment. The size of this fragment is shown on the left.

DETAILED DESCRIPTION OF THE INVENTION

Novel methods are provided for increasing the amount of mRNA spliced in a wild type fashion and/or wild type protein in cells or individuals using one or more compounds that alters the splicing of mRNA transcripts. In preferred embodiments, the ratio of wild-type to misspliced mRNA or wild type to mutant protein in a cell or individual is increased by administration of the one or more compounds. Methods of the invention can be used to prevent, manage, or treat disorders associated with missplicing. In preferred embodiments, the compound is a cytokinin, preferably a 6-(substituted amino) purine cytokinin, more preferably benzyladenine, most preferably kinetin. In other embodiments, the compound is one that increases production of properly spliced mRNA to a degree that is substantially similar to or greater than kinetin.

Disorders Treated with Methods of the Invention

The invention further relates to methods for altering the splicing of IKBKAP by contacting cells with a cytokinin, (preferably benzyladenine and more preferably kinetin). In particular, the invention relates to enhancing correct mRNA splicing in order to increase cellular levels of normal or wild type IKAP mRNA or protein encoded by a mutant IKBKAP gene in lymphoblast, fibroblast and neuronal cells. In specific embodiments, the invention relates to the use of kinetin for increasing the inclusion of exon 20 from the IKBKAP gene in spliced mRNA transcripts. In more specific embodiments, kinetin provides a treatment for individuals with FD by increasing the level of normal IKAP mRNA and protein.

The methods of the invention can be used to prevent, manage, or treat other disorders, in addition to FD, characterized by missplicing (see Table 1 for non-FD disorders). The missplicing in the other disorders may result from a mutation in i) the misspliced transcript, or ii) a component of the splicing machinery responsible for processing the misspliced transcript.

In a specifc embodiment, the non-FD disorder prevented, managed, or treated by the methods of the invention is NF1 caused by missplicing. NF1 gene splicing can be altered (e.g., to increase levels of wild type splicing) by contacting cells with a cytokinin, (preferably benzyladenine and more preferably kinetin).

TABLE 1

| Disorder | Misspliced mRNA transcript | Mutant gene |
|---|---|---|
| Neurofibromatosis 1 (NF1) | NF1 | NF1 |
| Neurofibromatosis 2 (NF2) | NF2 | NF2 |
| Familial isolated growth hormone deficiency type II (IGHD II) | growth hormone (GH-1) | growth hormone (GH-1) |
| Frasier syndrome | Wilms tumor suppressor gene (WT1) | Wilms tumor suppressor gene (WT1) |
| Frontotemporal demetia and Parkinsonism lined to Chromosome 17 (FTDP-17) | tau (MAPT) | tau (MAPT) |
| Atypical cystic fibrosis | cystic fibrosis transmembrane conductance regulator (CFTR) | cystic fibrosis transmembrane conductance regulator (CFTR) |
| Menkes Disease (MD) | ATP7A | ATP7A |
| Occipital Horn Syndrome | ATP7A | ATP7A |
| Myotonic dystrophy type 1 (DM1) | DM protein kinase (DMPK) | |
| Myotonic dystrophy type 2 (DM2) | ZNF9 | |

TABLE 1-continued

| Disorder | Misspliced mRNA transcript | Mutant gene |
|---|---|---|
| Retinitis pigmentosa (RP) | opsin | PRPF31, HRRP3, or PRPC8 |
| Spinal muscular atrophy (SMA) | Survivor of Motor Neuron gene 2 (SMN2) | |

This invention further provides methods for treating individuals at risk for developing a disorder associated with a misspliced mRNA transcript. In a preferred embodiments, the individual is at risk for developing familial dysautonomia or NF-1. Persons at risk for developing familial dysautonomia or NF1 may be identified by genetic screening for the presence of a mutation associated with familial dysautonomia (see e.g., International Patent Application No. PCT/US02/00473, filed Jan. 7, 2002, entitled: GENE FOR IDENTIFYING INDIVIDUALS WITH FAMILIAL DYSAUTONOMIA and which is incorporated herein by reference in its entirety) or NF-1 caused by missplicing (see e.g., U.S. Pat. Nos. 5,227,292, 5,605,799, 5,859,195, and 6,238,861). Accordingly, the compositions for use with the methods of this invention may be administered to an individual at various times during the course of the disease and during different degrees of expression of clinical symptoms. In a preferred embodiment, this invention provides methods and compositions for treating individuals with and at risk for developing the degenerative symptoms associated with familial dysautonomia, such as neuronal degeneration.

Compounds for Use in the Methods of the Invention

Compositions administered for the treatment of a disorder associated with a misspliced mRNA transcript can comprise one or more compounds that increase the amount of mRNA transcript spliced in a wild type manner and/or alter the ratio of wild type to misspliced mRNA transcripts. In preferred embodiments, at least one of the compounds in the composition is a cytokinin. In more preferred embodiment, the cytokinins are 6-(substituted amino)purine cytokinins. 6-(substituted amino)purine cytokinins include, but are not limited to, benzyladenine, kinetin, and 6-amino analogs thereof of Formula I:

Formula I in which $R_1$ is furfuryl, phenyl, benzyl, n-alkyl of 4, 5, or 6 carbons, branched alkyl of 4, 5, or 6 carbons, (cyclohexyl)methyl, 3,3-dimethylallyl, and 3-hydroxymethyl-3-methylallyl. Among the 6-(substituted amino)purine cytokinins that are intended to be used, singly or in combination, as a compound in the methods herein are kinetin, benzyladenine, isopentenyl adenine, (6-(3-hydroxymethyl-3-methylallyl)-aminopurine), 6-(3,3-dimethylallyl)aminopurine, 6-(benzyl) aminopurine, 6-(phenyl)aminopurine, 6-(n-alkyl) aminopurine, in which the n-alkyl group has 4, 5 or 6 carbons, and 6-(cyclohexyl)methylaminopurine. Most preferred is kinetin (6-(furfuryl)aminopurine). Other such 6-(substituted amine) purine cytokinins may be tested for the ability to improve proper mRNA splicing in cells in vitro.

In other preferred embodiments, the one or more cytokinins are administered to a subject in need thereof in combination with at least one other compound that provides a therapeutic effect. Examples of such other compounds include, but are not limited to, antioxidants (such as (−)-epigallocatechin gallate) and tocotrienols (such as α-tocotrienol, β-tocotrienol, γ-tocotrienol, and δ-tocotrienol). Such other compounds to be administered in combination with the one or more cytokinins may or may not be part of the same composition that comprises the one or more cytokinins.

The term "in combination" is not limited to the administration of the compounds at exactly the same time, but rather it is meant that the compounds are administered to a subject in a sequence and within a time interval such that they can act together to provide an increased benefit than if they were administered otherwise. For example, each compound may be administered at the same time or sequentially in any order at different points in time; however, if not administered at the same time, they should be administered sufficiently close in time so as to provide the desired therapeutic effect. Each compound can be administered separately, in any appropriate form and by any suitable route.

In various embodiments, the compounds are administered less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In preferred embodiments, two or more compounds are administered within the same patient visit.

Those compounds that improve proper mRNA splicing either by increasing the amount of wild type mRNA transcript and/or by increasing the ratio of wild-type to mutant mRNA or protein may be formulated as pharmaceuticals for administration to individuals or added to tissue culture medium at effective concentrations. Such concentrations are preferably about 0.1 ppm to about 500 ppm, preferably 10 ppm to about 100 ppm, in tissue culture medium and about 10 ppm to about 5000 ppm, preferably about 100 to about 1000 ppm, in pharmaceutical compositions. The precise concentrations, particularly for in vivo use, may be determined empirically and may be higher, particularly for in vivo use, depending upon the ability of the carrier or vehicle to deliver the compound or compounds to the treated cells or tissue and the manner in which compositions is contacted with the treated cells or tissue.

Identification of Compounds for Use in Methods of the Invention

The invention provides methods of screening for compounds that can alter splicing of a misspliced mRNA transcript, especially a mutant mRNA transcript that is misspliced. In a specific embodiment, the mutant mRNA transcript is a IKBKAP mRNA transcript. In a more specific embodiment, the a mutant IKBKAP mRNA transcript is present in a subject with FD. In an even more specific embodiment, the mutant IKBKAP mRNA transcript has the IVS20$^+$$_{6T \rightarrow C}$ mutation. In another specific embodiment, the mutant mRNA transcript is a NF1 mRNA transcript. In a more specific embodiment, the a mutant NF1 mRNA transcript is present in a subject with NF1.

Although not intending to be bound by a particular mechanism of action, a compound for use in the methods of the invention can alter the splicing of a misspliced mRNA by i) increasing wild type splicing of mutant mRNA transcripts, ii) decreasing mutant splicing of mutant mRNA transcripts, iii) increasing the amount of wild type splicing of wild type transcripts by mutant splicing machinery, and/or iv) decreasing the amount of mutant splicing of wild type mRNA transcripts by mutant splicing machinery. In other embodiments, compounds for use in the methods of the invention can alter the amount of mutant protein produced from either a i) mutant mRNA transcript or ii) wild type mRNA transcript spliced by mutant splicing machiniery. Although not intending to be bound by a particular mechanism of action, a compound for use in the methods of the invention can alter the amount of mutant protein produced from a misspliced mRNA transcript by i) increasing the translation of mRNA transcripts spliced in a manner consistent with wild type transcripts, ii) decreasing the translation of mRNA transcripts spliced in a manner inconsistent with wild type transcripts.

The methods of screening generally involve incubating a candidate compound with animals or cells that express a misspliced mRNA transcript and then assaying for an alteration in the splicing of the misspliced mRNA transcript thereby identifying a compound for use in the methods of the invention. The DNA comprising the gene which is misspliced may be endogenous or it may be heterologous, e.g., contained on a vector which has been inserted into the cell used in the assay such as by transfection or transduction or contained in a transgene which has been used to make a transgeneic. In embodiments where the DNA comprising the gene which is misspliced is heterologous, fragments of the full length gene may be used comprising at least the portion of the gene that is misspliced. In more specific embodiments, the fragment comprises exon 20 of IKBKAP.

In some embodiments, the amount of wild type spliced mRNA, mutant spliced mRNA, and/or both is determined. Any method known in the art can be used to assay for levels of mRNA transcripts, including, but not limited to, those assays to detect i) mRNA levels (e.g., by northern blots, RT-PCR, Q-PCR, etc.) or ii) protein levels (e.g., ELISA, western blots, etc.). In specific embodiments, an increase in the ratio of wild type mRNA transcripts to misspliced mRNA transcripts indicates that the compound decreases missplicing. In another specific embodiment, an increase in the ratio of wild type spliced mRNA transcripts to a control gene transcripts indicates that the compound decreases missplicing. In another specific embodiment, a decrease in the ratio of misspliced mRNA transcripts to a control gene transcripts indicates that the compound decreases missplicing. As used herein, the term "control gene" refers to a gene whose splicing or expression are not altered by any mutation that the animal or cell used in the assay may have or by contact of the candidate compound. Control genes may be endogenous (e.g. actin, etc.) or heterologous (e.g., a reporter gene such as luciferase, GFP, CAT, or β-galactosidase, ect.).

In other embodiments, the fragment of the misspliced gene comprising the portion that is misspliced may be part of a fusion protein with a reporter gene (e.g., luciferase, GFP, CAT, or β-galactosidase). Such a fusion protein will allow a signal from the reporter gene if the portion of the misspliced gene has been removed due to splicing. No signal or a reduced signal will be present from the reporter gene if the portion of the misspliced gene has not been removed due to splicing. If a candidate compound decreases missplicing, then the exon that is normally excluded due to missplicing will be included in the fusion protein and thus decrease the signal from the reporter gene. In a specific embodiment, the reporter gene comprises exon 20 of IKBKAP. In another specific embodiment, the reporter gene comprises exon 36 of NF1.

In some embodiments, expression of a misspliced mRNA transcript confers a phenotype to the animal or cell expressing the transcript that can be assayed (e.g., altered growth rate, longevity, behavior, etc.). Candidate compounds that can be used in the methods of the invention will cause a change in at least one of the misspliced mRNA transcript-associated phenotypes. In a preferred embodiment, the change in the misspliced mRNA transcript-associated phenotype is such that it approximates (or is substantially similar) to that of an organism or cell expressing a corresponding wild type mRNA transcript. In other embodiments, candidate compounds are assayed for their ability to alter the splicing of misspliced mRNA transcripts and/or alter misspliced mRNA transcript-associated phenotypes in a manner that is substantially similar to or better than compounds known to alter the splicing of misspliced mRNA transcripts in a therapeutically desirable way (e.g., cytokinins including kinetin). As used herein "substantially similar to" refers to a ratio of wild type to misspliced mRNAs and/or a misspliced mRNA transcript-associated phenotype that is more similar to that of a cell or organism i) expressing a wild type counterpart of the misspliced mRNA transcript or ii) expressing the misspliced mRNA transcript treated with a cytokinin (especially kinetin) than a cell or organism expressing the misspliced mRNA transcript and not treated with a cytokinin. Any animal model known in the art can be used to assay candidate compounds including, but not limited to, those described in Costa et al., 2002, Nature 415: 526-30 and Costa et al., 2001, Nat Genet. 27:399-405.

The screening methods of the invention also encompass the use of biochemical assays (e.g., in vitro transcription and/or translation assays) to identify compounds. Candidate compounds found to alter the splicing of misspliced mRNA in biochemical assays can then be assayed in animal or cell-based assays to determine any phenotype-altering properties.

The screening methods of the invention may be adapted for use in high throughput screen for compositions that can be effective for the treatment of disorders associated with missplicing of mRNA transcript(s), especially familial dysautonomia and NF1.

As used herein, the term "compound" refers to a molecule that has a desired biological effect. Compounds include, but are not limited to, proteinaceous molecules, including, but not limited to, peptide, polypeptide, protein, post-translationally modified protein, antibodies etc.; or a large molecule, including, but not limited to, inorganic or organic compounds; or a small molecule (less than 500 daltons), including, but not limited to, inorganic or organic compounds; or a nucleic acid molecule, including, but not limited to, double-stranded DNA, single-stranded DNA, double-stranded RNA, single-stranded RNA, or triple helix nucleic acid molecules. Compounds can be natural products derived from any known organism (including, but not limited to, animals, plants, bacteria, fungi, protista, or viruses) or from a library of synthetic molecules.

In one embodiment, a compound that decreases the amount of a misspliced mRNA transcript is identified by:
  a) contacting a cell or organism with a compound, wherein said cell or organism expresses said misspliced mRNA transcript; and
  b) determining the ratio of wild type to misspliced mRNA transcripts in said contacted cell or organism, wherein an increase in the ratio of wild type to misspliced mRNA transcripts of said contacted cell or organism as compared to the ratio of wild type to misspliced mRNA transcripts of a cell or organism expressing said misspliced mRNA transcript not contacted with the compound (i.e., a control cell or organism) indicates that the compound decreases the amount of said misspliced mRNA transcript.

In another embodiment, a compound that decreases the amount of a misspliced mRNA transcript is identified by:
  a) contacting a cell or organism with a compound, wherein said cell or organism expresses said misspliced mRNA transcript; and
  b) determining the ratio of wild type to misspliced mRNA transcripts in said contacted cell or organism, wherein the ratio of wild type to misspliced mRNA transcripts of said contacted cell or organism is substantially similar to the ratio of wild type to misspliced mRNA transcripts of a cell or organism expressing said misspliced mRNA transcript contacted with kinetin indicates that the compound decreases the amount of misspliced mRNA transcript.

In another embodiment, a compound that alters the amount of a misspliced mRNA transcript is identified by:
  a) contacting a cell or organism with a compound, wherein said cell or organism exhibits at least one phenotype that is altered as a result of its expression of said misspliced mRNA transcript when compared to a wild type cell or organism; and
  b) determining the phenotype of said contacted cell or organism, wherein a difference in the phenotype of said contacted cell or organism as compared to the phenotype of a cell or organism expressing said misspliced mRNA transcript not contacted with the compound (i.e., a control cell or organism) indicates that the compound alters the amount of said misspliced mRNA transcript.

In another embodiment, a compound that decreases the amount of a misspliced mRNA transcript is identified by:
  a) contacting a cell or organism with a compound, wherein said cell or organism exhibits at least one phenotype that is altered as a result of its expression of said misspliced mRNA transcript when compared to a wild type cell or organism; and
  b) determining the phenotype of said contacted cell or organism, wherein the phenotype of said contacted cell or organism is substantially similar to the phenotype of a cell or organism expressing said misspliced mRNA transcript contacted with kinetin indicates that the compound decreases the amount of misspliced mRNA transcript.

Treatment of Disorders Using Methods of the Invention

Disorders associated with misspliced mRNA can be prevented, managed, or treated by the methods of the invention. Individuals suffering from or likely to suffer from such a disorder are administered compositions comprising compounds that have a desired therapeutic effect (e.g., increasing the amount mRNA spliced in the wild type fashion). Disorders that can be treated by the methods of the invention include, but are not limited to, FD, NF1 cased by missplicing, and those disorders listed in Table 1. Compositions for the treatment of such disorders comprise one or more cytokinins at concentrations effective to produce a therapeutic effect. In preferred embodiments, at least one of the one or more cytokinins is a 6-(substituted amino)purine cytokinins. In more preferred embodiments, the 6-(substituted amino)purine cytokinin is kinetin or benzyladenine. Compositions administered to individuals in need thereof can further comprise other compounds that have a desired therapeutic effect including, but not limited to tocotrienols (e.g. 6-tocotrienol) and/or antioxidents (e.g., (−)-epigallocatechin gallate) in order to ameliorate or correct the adverse effects in an individual resulting from improperly spliced mRNA. In other embodiments, compositions for the treatment of disorders associated with missplicing comprise a therapeutically effect amount of a compound that increases production of properly spliced mRNA to a degree that is substantially similar to or greater than kinetin.

Compositions comprising compounds that have a desired therapeutic effect can also be administered to cells in vitro. Such cells in tissue culture provide a useful means for assessing the effectiveness of candidate compounds for increasing the ratio of wild type to mutant protein. Such cells may be either from tissue explants, or immortalized cell cultures. Examples of specific cell types include but are not limited to, lymphoblast, fibroblast and neuronal. The cells in culture can be bathed, suspended or grown in a culture medium used for mammalian cells. The medium contains an effective concentration of the composition comprising the compounds with therapeutic effect (e.g., one or more 6-(substituted amino) purine cytokinins selected from the group consisting of kinetin, benzyladenine, isopentenyl adenine, (6-(3-hydroxymethyl-3-methylallyl)-aminopyrine), 6-(3,3-dimethylallyl) aminopyrine, 6-(benzyl)aminopyrine, 6-(phenyl) aminopyrine, 6-(n-alkyl)aminopyrine, in which the n-alkyl group has 4, 5, or 6 carbons, 6-(cyclohexyl) methylaminopurine, and those compounds of Formula I, Formula I in which $R_1$ is furfuryl, phenyl, benzyl, n-alkyl of 4, 5, or 6 carbons, branched alkyl of 4, 5, or 6 carbons, (cyclohexyl) methyl, 3,3-dimethylallyl, and 3-hydroxymethyl-3-methylallyl). Preferred compounds, include, but are not limited to, kinetin and benzyladenine, most preferred is kinetin. A preferred concentration of the compounds of formula I in the medium is about 0.1 ppm to about 500 ppm, more preferably about 0.1 to 100 ppm, or a concentration of equivalent activity to a kinetin concentration of between about $10^{-6}$ M (1 μM or about 5 ppm) to about $5 \times 10^{-4}$ M (50 μM or about 250 ppm). For the most preferred cytokinin, kinetin, the more preferred concentration range is about 25 μM to about 250 μM or about 5 ppm to about 50 ppm in the culture medium. It is understood that the precise concentration for each 6-(substituted amino) purine cytokinin or mixture thereof may be empirically determined by testing a range of concentration and selecting those in which the ratio of wild-type to misspliced mRNA or protein is increased.

Additionally, such treated cells may be administered to an individual as ex vivo therapy either in addition to or instead of administration of a composition comprising the compounds with a desired therapeutic effect.

Administration

The compositions may be formulated in numerous forms, depending on the various factors specific for each patient (e.g., the severity and type of disorder, age, body weight, response, and the past medical history of the patient), the one or more compounds in the composition, the form of the compounds (e.g., in liquid, semi-liquid or solid form), and/or the route of administration (e.g., oral, intravenous, intramuscular, intra-arterial, intramedullary, intrathecal, intraventricular, transdermal, subcutaneous, intraperitoneal, intranasal, enteral, topical, sublingual, vaginal, or rectal means). Pharmaceutical carriers, vehicles, excipients, or diluents may be included in the compositions of the invention including, but not limited to, water, saline solutions, buffered saline solutions, oils (e.g., petroleum, animal, vegetable or synthetic oils), starch, glucose, lactose, sucrose, gelatin, malt, rice, flour, chalk, silica gel, sodium stearate, glycerol monostearate, talc, sodium chloride, dried skim milk, glycerol, propylene, glycol, ethanol, dextrose and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Oral compositions will generally include an inert diluent or an edible carrier and may be provided as a liquid suspension or solution or compressed into tablets or enclosed in gelatin capsules. For the purpose of oral therapeutic administration, the active compound or compounds can be incorporated with excipients and used in the form of solutions or suspensions, tablets, capsules or troches. The tablets, pills, capsules, troches and the like can contain any of the following ingredients, or compounds of a similar nature: a binder, such as microcrystalline cellulose, gum tragacanth and gelatin; an excipient such as starch and lactose, a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, and fruit flavoring. Further details on techniques for formulation and administration are provided in the latest edition of Remington's Pharmaceutical Sciences (Mack Publishing Co., Easton, Pa.).

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings and flavors. The active materials can also be mixed with other active materials which do not impair the desired action, or with materials that supplement the desired action.

Solutions or suspensions used for oral administration can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Liquid preparations can be enclosed in ampules, disposable syringes or multiple dose vials made of glass, plastic or other suitable material. Suitable carriers may include physiological saline or phosphate buffered saline (PBS), and the suspensions and solutions may contain thickening and solubilizing agents, such as glucose, polyethylene glycol, and polypropylene glycol and mixtures thereof. Liposomal suspensions, including tissue-targeted liposomes, may also be suitable as pharmaceutically acceptable carriers. These may be prepared according to methods known to those skilled in the art.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances, which increase the viscosity of the suspension, such as sodium carboxymethyl cellulose, sorbitol, or dextran. In addition, suspensions of the active compounds may be prepared as appropriate oily injection suspensions. Suitable lipophilic solvents or vehicles include fatty oils such as sesame oil, or synthetic fatty acid esters, such as ethyloleate or triglycerides, or liposomes. Optionally, the suspension may also contain suitable stabilizers or agents which increase the solubility of the compounds to allow for the preparation of highly concentrated solutions.

For topical or nasal administration, penetrants or permeation agents that are appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, and the like. Salts tend to be more soluble in aqueous solvents, or other protonic solvents, than are the corresponding free base forms.

Dosages

The compounds for use in the methods of the invention are present in compositions in an amount sufficient to have a therapeutic effect on the treated individual without serious toxic effects. The determination of an effective concentration or dose is well within the capability of those skilled in the art. The effective concentration or dose may be determined empirically by testing the compounds in individuals who would benefit from treatment, or using in vitro and in vivo systems, including tissue culture (e.g., using lymphoblast, fibroblast, or neuronal cells) or suitable animal models.

A therapeutically effective dose refers to that amount of a compound (e.g., cytokinin such as kinetin or other 6-(substituted amino) purine cytokinin) which prevents, ameliorates, reduces, or eliminates the symptoms of a disorder associated with a misspliced mRNA. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, which can be expressed as the ratio, ED50/LD50. Pharmaceutical compositions, which exhibit large therapeutic indices, are preferred. The data obtained from cell culture assays and animal studies are used in determining a range of dosages for human use. Preferred dosage contained in a pharmaceutical composition is within a range of circulating concentrations that include the ED50 with little or no toxicity. The dosage varies within this range depending upon the dosage form employed, sensitivity of the patient, and the route of administration.

The exact dosage will be determined by the practitioner, who will consider the factors related to the individual requiring treatment. Dosage and administration are adjusted to provide sufficient levels of the active compound or to maintain the desired effect of the active compound. Factors, which may be taken into account, include the severity of the individual's disease state, general health of the patient, age, weight, and gender of the patient, diet, time and frequency of administration, drug combination(s), reaction sensitivities, and tolerance/response to therapy. Guidance as to particular dosages and methods of delivery is provided in the literature and is generally available to practitioners in the art.

The concentration of active compound in the compositions will depend on absorption, inactivation, excretion rates of the active compound, the dosage schedule, and amount administered as well as other factors known to those of skill in the art. Typically a therapeutically effective dosage should deliver a concentration of at least about 10 ppm up to about 5000 ppm, preferably 50 ppm to about 1000 ppm, of the active compound to the treated individual. The active ingredient may be administered at once, or may be divided into a number of smaller doses to be administered at intervals of time. It is understood that the precise dosage of treatment is a function of individual being treated and may be determined empirically using known testing protocols or by extrapolation from in vivo or in vitro test data. It is to be further understood that for any particular individual, specific dosage regimens should be adjusted over time according to the individual need and the professional judgment of the medical personal administering or supervising the administration of the compositions, and that the concentration ranges set forth herein are exemplary only and are not intended to limit the scope or practice of the described compositions.

In certain embodiments, compositions are effective at concentrations of the 6-(substituted amino)purine cytokinin typically in the range of between about 0.1 ppm to about 100 ppm. When kinetin is used, the preferred concentration range is between about $10^{-6}$ M and $5 \times 10^{-4}$ M in the blood. At these concentrations, cytokinins, apparently have no or minimal toxic effect on mammalian cells in tissue culture. In embodiments where δ-tocotrienol is administered in combination with the one or more cytokinins, the preferred concentration range is between 0.25 μg/ml and 50 μg/ml in the blood. In embodiments where (−)-epigallocatechin gallate is administered in combination with the one or more cytokinins, the preferred concentration range is between 5 μg/ml and 60 μg/ml in the blood.

EXAMPLES

Materials and Methods

Patient cell lines. Patient lymphoblast cell lines previously established by EBV transformation were utilized. The cells have been previously described.[2,14]. Institutional Review Board approval had been obtained for the establishment and use of these lines through New York University Medical Center, Massachusetts General Hospital, and Harvard Medical School. Two fibroblast cell lines were also used. GUS12829 was established and has been previously described. GM02343 was purchased from the Coriell Cell Repository.

Drug Screen. The panel of 1040 independent compounds used was specifically designed for the NINDS sponsored Neurodegeneration Drug Screening Consortium (MicroSource Discovery Systems). A single FD lymphoblast cell line was cultured in 24 well format and treated with 10 μM compound dissolved in DMSO for 72 hours. RNA was extracted using Tri-Reagent™(Molecular Research Center) and reverse transcription and IKBKAP PCR was performed as previously described[4].

Cell Culture and Treatment. FD lymphoblast lines were grown in RPMI-1640 and primary fibroblast lines in Dulbecco's modified Eagle's media (DMEM) with Earle's balanced salts. Both media were supplemented with 2 mM L-gultamine and 1% penicillin/streptomycin and either 10% (lymphoblast) or 20% (fibroblast) fetal bovine serum (Invitrogen). Kinetin was obtained from both MicroSource Discovery Systems and Sigma and dissolved at 10 mM in either DMSO or water. FD cells were cultured in the presence of kinetin for 72 hours except where noted. Benzyladenine, zeatin, and 2iP were obtained from Sigma and dissolved in DMSO at 10 mM. These compounds were tested at concentrations of 1 μM, 10 μM, 50 μM, and 100 μM. Cycloheximide was obtained from Sigma and dissolved at 10 mg/ml in DMSO. Cells were treated with 100 μM kinetin for eight hours, then 50 μg/ml cycloheximide was added to the cultures for four hours[16].

Determination of IKBKAP transcript ratios. The ratio of WT:MU IKBKAP transcripts was determined following amplification by fractionation on 1.5% agarose gels stained with ethidium bromide[4]. Each gel band was assessed using an Alpha 2000™ Image Analyzer and software coupled with automatic background subtraction (Alpha Innotech Corporation). WT:MU ratios were obtained using the integrated density value (IDV) for each band[4]. Real-time quantitative PCR (QPCR) was performed as described using primers specific to WT IKBKAP, MU IKBKAP, and 18S ribosomal RNA[4]. In order to assess total IKBKAP expression the following primers were used: EX3F-5'-TCAGGACTTGCTGGATCAGGA (SEQ ID NO:1) and EX4R-5'-CCACTGGCTACACTCCCT-TCT (SEQ ID NO:2) located in IKBKAP exons 3 and 4 and an exon 3 TaqMan probe: TCTGGAGACGTCATACTCTG-CAGTCTCAGC (SEQ ID NO:3). For the Myosin VA assay, primers were designed that flank the alternatively spliced exon 31 in order to assess transcript levels of the two isoforms. Primer sequences were as follows: MYO-F: GAA TAC AAT GAC AGA TTC CAC (SEQ ID NO:4); MYO-R: CAG GCT GGC CTC AAT TGC (SEQ ID NO:5). Following reverse-transcription and PCR, products were separated on a 1.5% agarose gel and IDV ratios determined as described above.

Western Blot Analysis. Patient lymphoblast cell lines were treated with increasing concentrations of kinetin for 72 hours. Extracted protein was run on a 6% polyacrylamide gel. The samples were transferred to nitrocellulose and stained with Ponceau-S to visualize protein loading. IKAP was detected using a monoclonal antibody raised against amino acids 796-1008 of IKAP (BD Bioscience) that detects the 150 kD full-length IKAP protein. The same blot was probed with an antibody to insulin-degrading enzyme (IDE) as a protein loading control. Bands were quantitated using an Alpha 2000™ Image Analyzer.

In vivo IKBKAP minigene splicing assay. IKBKAP genomic DNA was amplified from an unaffected and an FD individual using primers in exon 19 and 21: EX19F-5'-CAT-TACAGGCCGGCCTGAG (SEQ ID NO:6) and EX21R -5'-CAGCTTAGAAAGTTACCTTAG (SEQ ID NO:7). The amplified products were cloned into pcDNA3.1/V5-His Topo (Invitrogen) and sequenced for verification. HEK293 cells were plated and kinetin was added to the tissue culture media 4 hours later. Minigene constructs were transiently transfected 12 hours later using Genejuice (Novagen) as directed by the manufacturer. After 48 hours RNA was isolated using the RNAeasy kit (Qiagen) and reverse transcribed using Superscript™ II reverse transcriptase (Invitrogen) as described[4]. PCR was performed using vector specific primers: T7 (TAATACGACTCACTATAGG) (SEQ ID NO:8) and BGHR (TAGAAGGCACAGTCGAGG) (SEQ ID NO:9), which amplify both WT and MU transcripts, or the MU specific primer EX19/21F (CAAAGCTTGTATTACA-GACT) (SEQ ID NO:10) and BGH-R to specifically amplify only MU transcripts. PCR was performed as follows: 26 cycles of [94° C., 30 s; 56° C., 30 s; 72° C., 30 s] and products resolved on a 1.5% agarose gel and visualized by ethidium bromide staining.

Example 1

IKBKAP mRNA Ratio Analysis

An assay that provides stable and consistent measurement of the ratio of WT:MU FD IKBKAP mRNA splice products in lymphoblast cell lines was developed[4]. This assay was employed as part of the Neurodegeneration Drug Screening Consortium[7] to identify compounds that increase the relative production of WT mRNA. A single, standard FD lymphoblast cell line was assayed after 72 hours in the presence of 10 μM test drug, using compounds dissolved in DMSO. A panel of 1040 bioactive compounds (NINDS Custom Collection, MicroSource Discovery Systems) were screened, most of which have been approved for use by the Food and Drug Administration (FDA). Prior to initiating the screen, it was confirmed that DMSO had no effect on IKBKAP splicing and was not toxic to the cells at the test concentration of 0.1%. One compound, kinetin (6-furfurylaminopurine) (FIG. 1b), dramatically enhanced correct splicing in FD cells at the test concentration of 10 μM (FIG. 1c).

Figure 2:
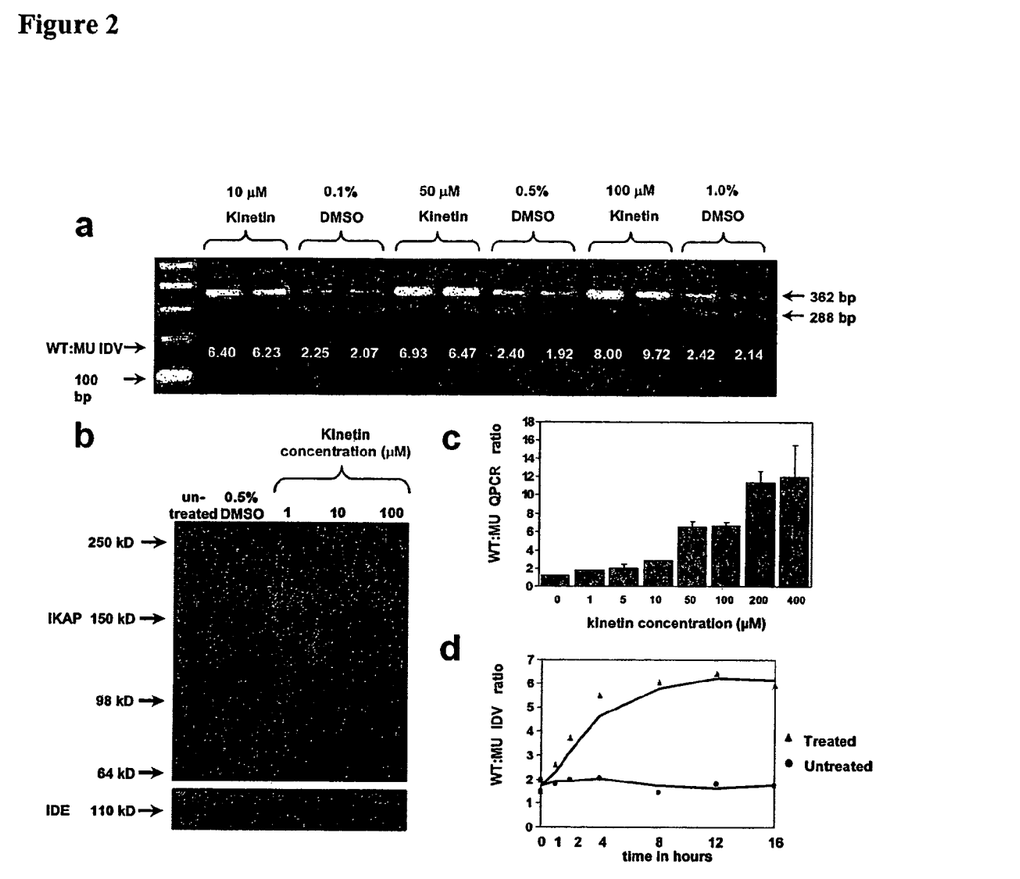
FIG. 2 The action of kinetin on IKBKAP splicing is dose and time dependent and results in an increase of IKAP protein in FD lymphoblast cell lines. (a) RT-PCR demonstrating increasing WT:MU IKBKAP ratios as a result of increased kinetin concentration. Sizes of the WT and MU bands are shown on the right, and the IDV ratios are shown beneath each lane. (b) Western blot probed with an IKAP monoclonal antibody showing that increasing concentrations of kinetin result in an increase in IKAP protein production in FD cells. The lower panel shows the same blot probed with an IDE antibody as a protein loading control. (c) Graph of WT:MU IKBKAP ratios at increasing kinetin concentrations determined by QPCR of FD cells (treated with kinetin in water in duplicate and each amplified in triplicate) showing that higher doses of kinetin continue to increase WT:MU IKBKAP. Examination of panel (a) shows that at kinetin concentrations of 100 μM the MU band is barely discernable using densitometry, therefore QPCR was used for this study. (d) Graph of WT:MU ratios generated using IDV values following culturing of FD cells in 50 μM kinetin for increasing lengths of time. All treatments were performed in duplicate and average data points are plotted.

Concentrations of kinetin up to 100 μM were tested and significant enhancement of WT IKBKAP production with increasing concentration in two independent FD lymphoblast lines was observed (FIG. 2a). The increase in WT:MU mRNA was mirrored by an increase in production of IKAP protein (FIG. 2b), confirming the increased production of functional WT mRNA. To avoid DMSO toxicity at higher concentrations, kinetin was purchased from an independent source (Sigma) and dissolved in water. Real-time quantitative PCR analysis showed that the WT:MU IKBKAP mRNA ratio increased steadily from approximately 1:1 in untreated cells to 12:1 in cells treated with 400 μM kinetin, the maximum dose tested due to the appearance of some cellular toxicity (FIG. 2c). By contrast, total IKBKAP mRNA was relatively unaffected, with a slight increase (~1.5 fold) being detected only at doses higher than 50 μM (data not shown). In an FD lymphoblast assay, neither zeatin nor 2iP (dissolved in DMSO at 10 mM) had any effect on WT:MU IKBKAP ratio. Benzyladenine did enhance inclusion of exon 20 in the IKBKAP transcripts approximately 2-fold by 100 μM, a less dramatic effect than kinetin. The fact that only kinetin and benzyladenine alter IKBKAP splicing suggests that the nature of the adenine $N^6$-linked modification plays a role in this function.

To define how quickly kinetin has its effect on IKBKAP splicing, a time-course at 50 μM kinetin was performed (FIG. 2d). The increase in the WT:MU ratio was seen at one hour, was maximal by 8 hours, and was maintained for at least 72 hours in culture without kinetin replenishment. The consistency of the effect was tested by treating lymphoblast lines from nine FD patients with 50 μM kinetin for 24 hours. All nine lines showed an increase in WT IKBKAP mRNA with WT:MU ratios ranging from 1.3-1.9 in untreated cells to 5.6-8.6 in kinetin treated cells. Kinetin was also effective in FD fibroblast lines which exhibited a dose-dependent increase in WT:MU IKBKAP ratio similar to that seen in lymphoblasts.

Example 2

MYO5A mRNA Ratio Analysis

Figure 3:
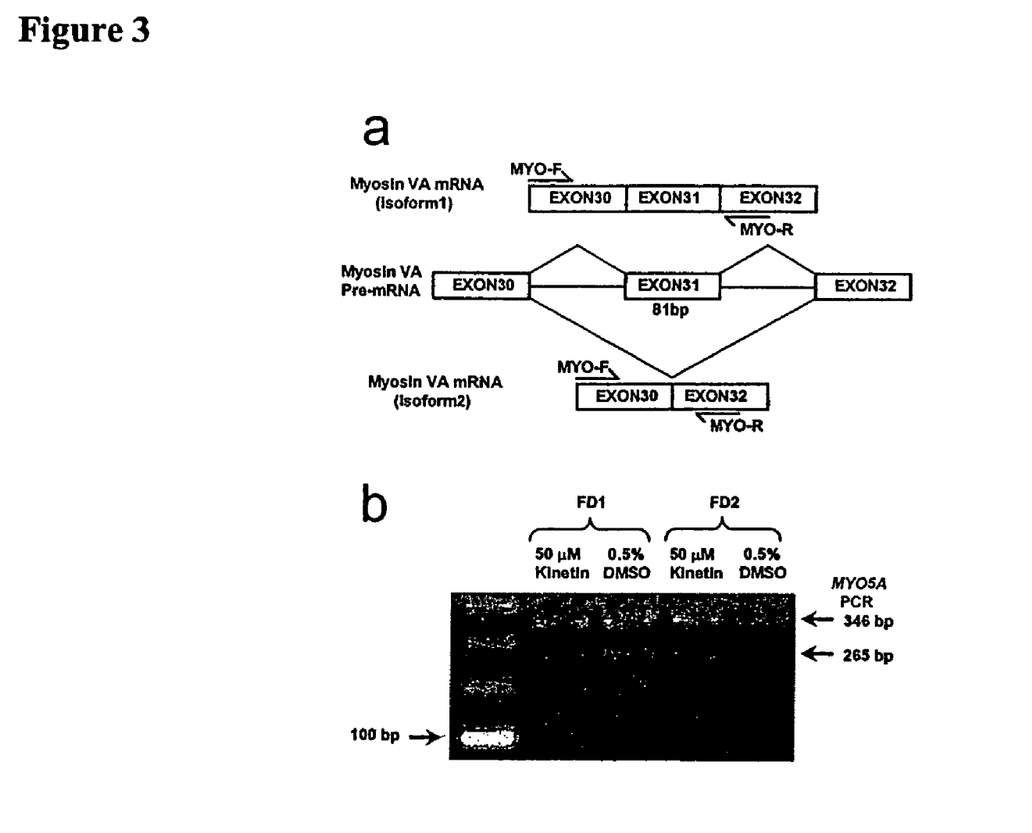

To explore whether the effect of kinetin was specific to IKBKAP exon 20 or generally increased inclusion of alternatively spliced exons, splicing of the MYO5A gene was assayed (FIG. 3a). MYO5A expresses multiple isoforms in fibroblasts and lymphoblasts, one of which is generated by skipping of exon 31[10]. Primers flanking exon 31 were designed. The ratio of the two MYO5A isoforms in nine FD lymphoblast cell lines following treatment with 50 µM kinetin for 72 hours was examined. No significant difference was observed in the ratio of the two isoforms between the treated and untreated samples, with average transcript ratios of 2.33 and 2.46, respectively (FIG. 3b).

Example 3

IKBKAP Nonsense Mediated Decay Analysis

Figure 4:
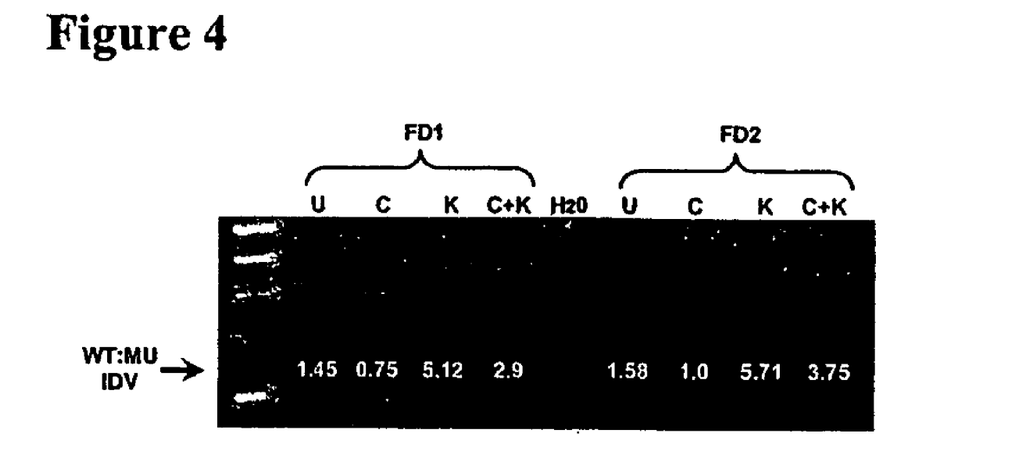
FIG. 4 Kinetin increases WT:MU IKBKAP transcript ratio in the presence or absence of nonsense mediated decay (NMD) of the mutant transcript. Two FD lymphoblast cell lines, FD1 and FD2, were untreated (U) or treated with 50 μg/ml cycloheximide (C) to inhibit NMD, 100 μM kinetin (K), or cycloheximide+kinetin (C+K). RT-PCR amplification and fractionation of the amplified product on a 1.5% agarose gel was performed on cell extracts. WT:MU IKBKAP transcript ratios were determined using the integrated density value (IDV) obtained for each band and are shown beneath each lane. Primer sequences and PCR conditions have been previously described[4]

The $IVS20^{+6T \rightarrow C}$ mutation in IKBKAP leads to a frameshift and a premature termination codon in exon 21, which is expected to target the mutant transcript for decay via the nonsense-mediated mRNA decay (NMD) pathway[15]. To exclude the possibility that the observed changes in the WT:MU transcript ratio in the presence of kinetin were due to increased NMD of the mutant transcript rather than direct action of kinetin on IKBKAP splicing, the WT:MU transcript ratio was assayed in the absence of NMD. FD cells were exposed to cycloheximide, a translation inhibitor, to inhibit NMD of the mutant transcript[16]. FD cells treated with cyclohexamide alone increased mutant transcript levels thereby decreasing the WT:MU transcript ratio as expected (FIG. 4). However, FD cells treated kinetin in the presence of cycloheximide significantly altered the WT:MU transcript ratio in a manner similar to that of kinetin treatment alone (FIG. 4). Thus, the observed decrease in the WT:MU transcript ratio in kinetin-treated FD cells is not dependent on NMD-mediated destruction of the mutant transcript, but rather is due to kinetin's action on IKBKAP splicing.

Example 4

IKBKAP Minigene Analysis

Figure 5:
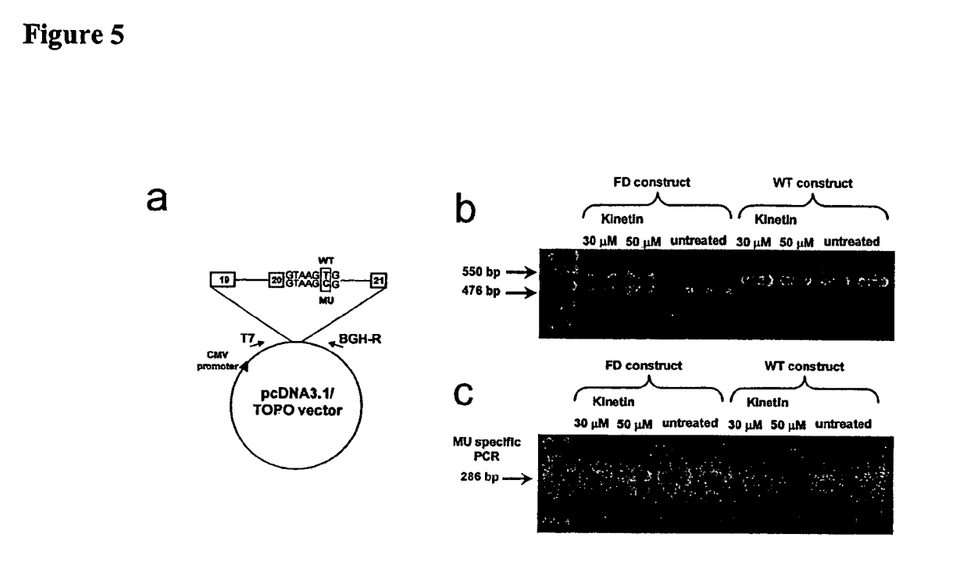

For studies aimed at understanding the mechanism of action of kinetin on IKBKAP splicing, both FD and WT minigene constructs containing the genomic sequence spanning exon 19 to 21 were created (FIG. 5a). These constructs were transfected into HEK293 cells and RNA was amplified using vector-specific primers to avoid amplification of the endogenous IKBKAP message. Evaluation of the transcripts produced from the WT construct showed that although the WT transcript is the predominant product, trace levels of exon 20 skipping do occur even in the absence of the FD mutation. Introduction of the FD mutation into the construct increased exon 20 skipping as predicted. Interestingly, treatment with kinetin enhanced inclusion of exon 20 not only in the FD construct, but also in the WT construct (FIG. 5B). In fact, utilization of a MU-specific PCR assay[4] revealed that exon 20 skipping is completely corrected in transcripts generated from the WT construct by kinetin treatment (FIG. 5c). These findings indicated that the ability of kinetin to enhance splicing efficiency is not dependent on either the presence of the FD mutation or the wider regulation of IKBKAP transcription or IKAP protein production, and is likely due to specific sequence elements in the region of exon 20 that function to regulate splicing of this particular exon.

Example 5

SMN1 and MYO5A Analysis

Comparison of SMN1 and SMN2, closely related genes involved in spinal muscular atrophy (SMA), has shown that a single DNA change in the coding sequence results in skipping of exon 7 in SMN2[11,12]. It has been reported that aclarubicin treatment can promote the inclusion of exon 7 in the SMN2 transcript[13]. Aclarubicin was tested on FD cells as part of our original screen and had no effect on IKBKAP splicing. Similarly, kinetin has no effect on skipping of exon 7 in SMN2 (Jianhua Zhou). Further, neither of these drugs promotes inclusion of alternatively spliced exons in MYO5A[13]. Taken together, these studies clearly indicate that there are multiple distinct mechanisms that contribute to exon choice during pre-mRNA splicing in both normal and disease situations. The distinctive tissue-specific splicing pattern seen in FD and the known importance of tissue-specific alternative splicing in generating protein diversity add yet another level of complexity to this important regulatory process.

Example 6

Clinical Assessment for Treatment of Familial Dysautonomia

Kinetin Drug Absorption Study. A drug absorption study is performed on approximately 50 individuals. The individuals are given a dose of kinetin Serum levels are obtained at various time points, 0 15 min, 30 min, 60 min and 120 min, to determine clearance.

The assessment is an unblinded and longitudinal study where each patient is his or her own control. However, a blinded assessment with a placebo control could also be performed. A daily dose of kinetin is given for individuals diagnosed with FD whose weight is greater than 25 kg. Dosages are calculated based on drug absorption assessment. An initial dose is calculated according to patient's weight and is administered orally, via a gastrointestinal tube or sublingually, preferably orally. Blood samples will be taken at baseline (0 min), 15 min, 30 min and then one hour and 2 hours post administration to assess blood level.

During the study, individuals are assessed at various time periods, including an initial visit, a visit at 1 month, 6 months, 12 months, 18 months, 24 months and 36 months. Activities that occur at the various visits include functional assessment, determination of the wild-type to mutant ratio of mRNA IKAP or protein IKAP, sensory and gait tests, autonomic (CV and eye) tests and autonomic (EGG).

The functional assessment of the individuals is based on a score from 0 (normal) to 15 (globally severely limited). The individuals oral intake, crisis frequency, cognitive ability, speech and gait are assessed.

In addition, blood tests are conducted to assess the mRNA IKAP ratio (wildtype:mutant) from isolated lymphoblasts. The ratio of wild type to mutant protein may also be assessed using methods well known in the art in combination with the methods described above. Alternatively or additionally, other tissue types may be obtained by biopsy, including but not limited to a skin punch test, to assess the mRNA or protein IKAP wild type to mutant ratio found in fibroblasts.

Sensory assessments are also performed. The sensory assessments may include the following: a histamine test (with photograph and measurement an appropriate time), a pain test (sharp vs. dull)*, a temperature assessment (hot and cold thresholds using Thermotest by Nicolet)*, vibration thresholds (using biothesiometer)*, and deep tendon reflexes. (Items with * can only be done in patients over 6 years).

Autonomic assessments are also performed. The autonomic assessments may include cardiovascular tests, including tilt test, heart rate variability, sympathovagal balance, and autonomic perturbations. More specifically the tilt test includes blood pressure, mean blood pressure and heart rate while the individual is first supine and then erect for a short and longer period of time. The heart rate variability test is performed supine and erect and uses the Nicolet MMP program. The sympathovagal balance test* is performed supine and erect and uses ANSAR technology which provides SDNN and PN50 values (measures of sympathetic and parasympathetic tone, respectively). The autonomic perturbations* include deep breathing and valsalva, and tilt to assess sympathovagal responsiveness (data attained via Atlas technology). Autonomic assessment also includes an ophthalmologic test—the Schirmer tear test. In addition, the autonomic assessment includes gastrointestinal testing comprising a electrogastrogram with water load.

The extent of a response to treatment is based on a positive change in any objective measure of clinical symptom or biochemical marker during treatment. Such biochemical marker may include a change in protein or a change in mRNA ratio of wild type to mutant IKAP.

Clinical symptoms are assessed according to any method known in the art including Hilz et al., 1998, Journal Neurology, Neurosurgery, and Psychiatry 65:338-343; Pearson and Pytel, 1978, J Neurol Sci 39: 123-130; Axelrod, 1996, Autonomic and Sensory Disorders. In: *Principles and Practice of Medical Genetics. 3rd edition*, Emory and Rimoin eds. Churchill Livingstone, Edinburgh. pp 397-411; Axelrod, 2002, Clin Auton Res 12:2-14; Axelrod and Maayan, Familial Dysautonomia. In: Burg et al, eds, *Gellis and Kagan's Current Pediatric Therapy, 17th edition* WB Saunders, Philadelphia, 2002, pp 437-441; Brown et al., 2003, Clinical Science 104:163-9; Maayan et al., 1987, J. Auton Nerv. Syst. 21:51-8; Marthol et al., 2003, Eur. J. Clin. Invest. 33:912-8; Cuajungco et al., 2003, AM J Hum Genet. 72:749-58.

Absorption studies and symptom assessment are further conducted with kinetin in combination with δ-tocotrienol and/or (−)-epigallocatechin gallate.

Example 7

NF1 Minigene Analysis

For studies aimed at understanding the mechanism of action of kinetin on NF1 splicing, both NF1 and WT minigene constructs containing the genomic sequence spanning exons 35 to 37 of the NF1 gene were created. NF1 genomic DNA was amplified from an unaffected and an NF1 individual using primers at the 5' end of exon 35 and the 3' end of exon 37. The NF1 individual had a C>T mutation at nucleotide residue position 6724 of the NF1 cDNA. The amplified products were cloned into pcDNA3.1/V5-His Topo (Invitrogen) and sequenced for verification. HEK293 cells were plated and kinetin was added to the tissue culture media 4 hours later. Minigene constructs were transiently transfected 12 hours later using Genejuice (Novagen) as directed by the manufacturer. After 48 hours RNA was isolated using the RNAeasy kit (Qiagen) and reverse transcribed using Superscript™ II reverse transcriptase (Invitrogen) as described[4]. PCR was performed using vector specific primers: T7 (TAATAC-GACTCACTATAGG) (SEQ ID NO:8) and BGHR (TAGAAGGCACAGTCGAGG) (SEQ ID NO:9), which amplify both WT and MU transcripts. PCR was performed as follows: 30 cycles of [94° C., 30 s; 58° C., 30 s; 72° C., 30 s] and products resolved on a 1.5% agarose gel and visualized by ethidium bromide staining.

When treated with kinetin, cells transfected with the NF1 minigene had altered splicing as compared to cells transfected with the NF1 minigene in the absence of kinetin. One of skill in the art could determine if the alteration in splicing resulted in more wild type and/or less mutant splicing to occur using well known molecular biological techniques.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference. The invention now being fully described, it will be apparent to one of ordinary skill in the art that many changes and modifications can be made thereto without departing from the spirit or scope of the appended claims.

REFERENCES

1. Nissim-Rafinia, M. & Kerem, B. Splicing regulation as a potential genetic modifier. *Trends Genet* 18, 123-7 (2002).
2. Slaugenhaupt, S. A. et al. Tissue-specific expression of a splicing mutation in the IKBKAP gene causes familial dysautonomia. *Am J Hum Genet* 68, 598-605 (2001).
3. Anderson, S. L. et al. Familial dysautonomia is caused by mutations of the IKAP gene. *Am J Hum Genet* 68, 753-8 (2001).
4. Cuajungco, M. P. et al. Tissue-Specific Reduction in Splicing Efficiency of IKBKAP Due to the Major Mutation Associated with Familial Dysautonomia. *Am J Hum Genet* 72, 749-58 (2003).
5. Maayan, C., Kaplan, E., Shachar, S., Peleg, O. & Godfrey, S. Incidence of familial dysautonomia in Israel 1977-1981. *Clin Genet* 32, 106-8 (1987).
6. Leyne, M., Mull, J., Gill, S. P., Cuajungco, M. P., Oddoux, C., Blumenfeld, A., Maayan, C., Gusella, J. F., Axelrod, F. B., Slaugenhaupt, S. A. Identification of the first non-Jewish mutation in Familial Dysautonomia. *Am J Med Genet* In Press (2003).
7. Heemskerk, J., Tobin, A. J. & Bain, L. J. Teaching old drugs new tricks. Meeting of the Neurodegeneration Drug Screening Consortium, 7-8 Apr. 2002, Washington, D.C., USA. *Trends Neurosci* 25, 494-6 (2002).
8. Rattan, S. I. & Clark, B. F. Kinetin delays the onset of ageing characteristics in human fibroblasts. *Biochem Biophys Res Commun* 201, 665-72 (1994).
9. Olsen, A., Siboska, G. E., Clark, B. F. & Rattan, S. I. N(6)-Furfuryladenine, kinetin, protects against Fenton reaction-mediated oxidative damage to DNA. *Biochem Biophys Res Commun* 265, 499-502 (1999).

10. Lambert, J., Naeyaert, J. M., Callens, T., De Paepe, A. & Messiaen, L. Human myosin V gene produces different transcripts in a cell type-specific manner. *Biochem Biophys Res Commun* 252, 329-33 (1998).
11. Lorson, C. L., Hahnen, E., Androphy, E. J. & Wirth, B. A single nucleotide in the SMN gene regulates splicing and is responsible for spinal muscular atrophy. *Proc Natl Acad Sci USA* 96, 6307-11 (1999).
12. Monani, U. R. et al. A single nucleotide difference that alters splicing patterns distinguishes the SMA gene SMN1 from the copy gene SMN2. *Hum Mol Genet* 8, 1177-83 (1999).
13. Andreassi, C. et al. Aclarubicin treatment restores SMN levels to cells derived from type I spinal muscular atrophy patients. *Hum Mol Genet* 10, 2841-9 (2001).
14. Blumenfeld, A. et al. Precise genetic mapping and haplotype analysis of the familial dysautonomia gene on human chromosome 9q31. *Am J Hum Genet* 64, 1110-8 (1999).
15. Frischmeyer, P. A. and Dietz, H. C. (1999) Nonsense-mediated mRNA decay in health and disease. *Hum. Mol. Genet.* 8, 1893-1900.
16. Noensie, E. N. and Dietz, H. C. (2001) A strategy for disease gene identification through nonsense-mediated mRNA decay inhibition. *Nat. Biotechnol.* 19, 434-439.

---

The invention claimed is:

1. A method to increase a ratio of wild type IKBKAP mRNA to misspliced IKBKAP mRNA in human cells, wherein said misspliced IKBKAP mRNA is transcribed from a mutant IKBKAP gene which expresses wild type and misspliced IKBKAP mRNA, which mutant IKBKAP gene includes the IVS20$^{+6T \rightarrow C}$ mutation, said comprising contacting cells possessing said mutant IKBKAP gene with kinetin in an amount effective to increase said ratio of wild type mRNA to misspliced mRNA in said cells.

2. The method according to claim 1, wherein said cells are neuronal cells.

3. The method according to claim 1, wherein said cells possessing the mutated IKBKAP gene are from an individual with Familial Dysautonomia.

4. A method to alter IKBKAP mRNA splicing in human cells, wherein said IKBKAP mRNA is transcribed from a mutant IKBKAP gene which expresses wild type and mutant IKBKAP mRNA, which mutant IKBKAP gene includes the IVS20$^{+6T \rightarrow C}$ mutation, said method comprising contacting cells possessing said mutant IKBKAP gene with kinetin in an amount effective to alter said IKBKAP mRNA splicing in said cells.

5. The method according to claim 4, wherein said cells are neuronal cells.

6. The method according to claim 4, wherein said cells possessing the mutated IKBKAP gene are from an individual with Familial Dysautonomia.

7. A method to increase inclusion of spliced transcripts of exon 20 in IKBKAP mRNA in human cells, wherein said IKBKAP mRNA is transcribed from a mutant IKBKAP gene which expresses wild type and misspliced IKBKAP mRNA and wherein said misspliced IKBKAP mRNA skips exon 20, which mutant IKBKAP gene includes the IVS20$^{+6T \rightarrow C}$ mutation, said method comprising contacting cells possessing said mutant IKBKAP gene with kinetin in an amount effective to increase said inclusion of exon 20 in spliced transcripts.

8. The method according to claim 7, wherein said cells are neuronal cells.

9. The method according to claim 7, wherein said cells possessing the mutated IKBKAP gene are from an individual with Familial Dysautonomia.

10. A method to increase a ratio of wild type IKBKAP mRNA to misspliced IKBKAP mRNA in a human subject having a mutant IKBKAP gene that includes the IVS20$^{+6T \rightarrow C}$ mutation, said method comprising administering to said human subject kinetin in an amount effective to increase said ratio of wild type mRNA to misspliced mRNA in said human subject.

* * * * *

SEQUENCE LISTING

<160> NUMBER OF SEQ ID NOS: 10

<210> SEQ ID NO 1
<211> LENGTH: 21
<212> TYPE: DNA
<213> ORGANISM: human

<400> SEQUENCE: 1
tcaggacttg ctggatcagg a                                      21

<210> SEQ ID NO 2
<211> LENGTH: 21
<212> TYPE: DNA
<213> ORGANISM: human

<400> SEQUENCE: 2
ccactggcta cactcccttc t                                      21

<210> SEQ ID NO 3
<211> LENGTH: 30
<212> TYPE: DNA
<213> ORGANISM: human

<400> SEQUENCE: 3
tctggagacg tcatactctg cagtctcagc                             30

<210> SEQ ID NO 4
<211> LENGTH: 21
<212> TYPE: DNA
<213> ORGANISM: human

<400> SEQUENCE: 4
gaatacaatg acagattcca c                                      21

<210> SEQ ID NO 5
<211> LENGTH: 18
<212> TYPE: DNA
<213> ORGANISM: human

<400> SEQUENCE: 5
caggctggcc tcaattgc                                          18

<210> SEQ ID NO 6
<211> LENGTH: 19
<212> TYPE: DNA
<213> ORGANISM: human

<400> SEQUENCE: 6
cattacaggc cggcctgag                                         19

```
<210> SEQ ID NO 7
<211> LENGTH: 21
<212> TYPE: DNA
<213> ORGANISM: human

<400> SEQUENCE: 7
cagcttagaa agttacctta g                                              21

<210> SEQ ID NO 8
<211> LENGTH: 19
<212> TYPE: DNA
<213> ORGANISM: artificial
<220> FEATURE:
<223> OTHER INFORMATION: vector

<400> SEQUENCE: 8
taatacgact cactatagg                                                 19

<210> SEQ ID NO 9
<211> LENGTH: 18
<212> TYPE: DNA
<213> ORGANISM: artificial
<220> FEATURE:
<223> OTHER INFORMATION: vector

<400> SEQUENCE: 9
tagaaggcac agtcgagg                                                  18

<210> SEQ ID NO 10
<211> LENGTH: 20
<212> TYPE: DNA
<213> ORGANISM: artificial
<220> FEATURE:
<223> OTHER INFORMATION: novel

<400> SEQUENCE: 10
caaagcttgt attacagact                                                20
```